US005705928A

United States Patent [19]

Haner et al.

[11] Patent Number: 5,705,928
[45] Date of Patent: Jan. 6, 1998

[54] SAMPLE DELIVERY SYSTEM USED IN CHEMICAL ANALYSIS METHODS WHICH EMPLOYS PRESSURIZED GAS FOR SAMPLE CONVEYANCE

[75] Inventors: Ronald L. Haner, San Francisco; Christopher C. Kellogg, Walnut Creek, both of Calif.; David W. Duff, Ipswich, Mass.

[73] Assignee: Varian Associates, Inc., Palo Alto, Calif.

[21] Appl. No.: 665,165

[22] Filed: Jun. 14, 1996

[51] Int. Cl.⁶ .................................................. G01V 3/00
[52] U.S. Cl. ...................................... 324/321; 324/320
[58] Field of Search ............................. 324/321, 320, 324/319, 318, 309, 307, 306

[56] References Cited

U.S. PATENT DOCUMENTS

| | | | |
|---|---|---|---|
| 4,581,583 | 4/1986 | Van Vliet et al. | 324/321 |
| 5,146,166 | 9/1992 | Bartuska | 324/321 |
| 5,200,702 | 4/1993 | Lilly et al. | 324/321 |
| 5,534,780 | 7/1996 | Lilly | 324/321 |

*Primary Examiner*—Louis M. Arana
*Attorney, Agent, or Firm*—Edward H. Berkowitz

[57] ABSTRACT

A sample delivery system for a flow-through NMR analysis is provided, which utilizes pressurized gas as a means for conveying a sample into and out of an NMR spectrometer. Two sources of gas pressure, a forward pressure and back pressure, oppose the sample within the tubing of the sample delivery system and the tubing of the flow-through system which are operatively coupled together. Conveyance of the sample in any direction within the tubing is achieved by adjusting the pressure differential. Precise positioning of the sample in the magnetic field center and complete removal of the sample from the NMR spectrometer when analysis is complete are achieved by using a signal processor which receives signals from the NMR detector or other detectors positioned along the length of the tubing. These signals provide an indication of the position of the sample in the tubing. The signal processor uses this information to adjust the forward and back pressure, thereby achieving the desired positioning of the sample.

17 Claims, 8 Drawing Sheets

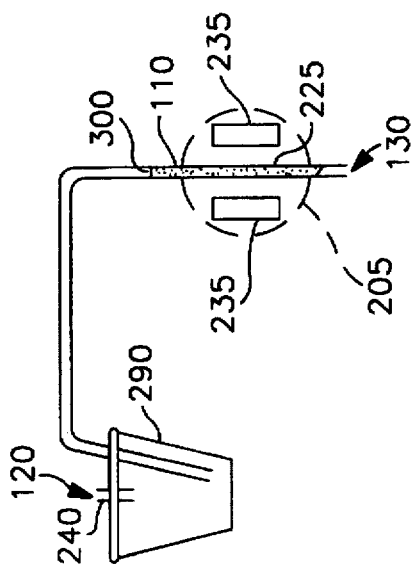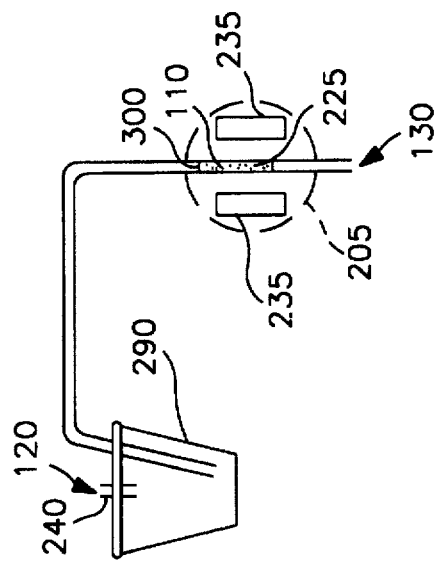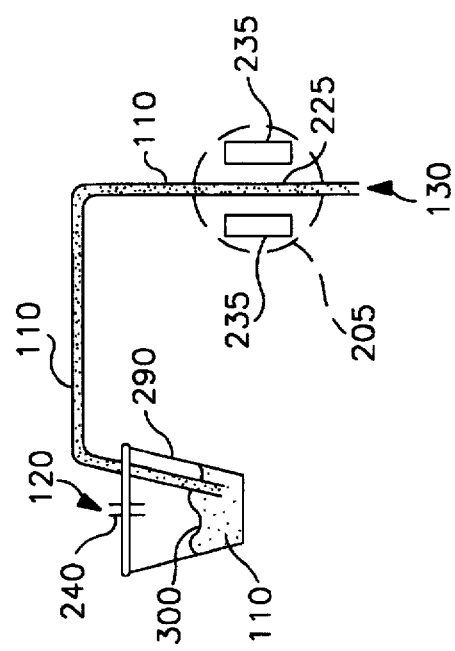
FIG. 3B
FIG. 3C
FIG. 3A

SAMPLE DELIVERY SYSTEM USED IN CHEMICAL ANALYSIS METHODS WHICH EMPLOYS PRESSURIZED GAS FOR SAMPLE CONVEYANCE

FIELD OF THE INVENTION

The invention in general relates to the field of chemical analysis, more particularly to the field of sample delivery systems which are used to transport a sample to be analyzed into and then out of an analyzing instrument. Specifically, the invention relates to a sampling system which conveys a liquid sample to be analyzed through an analyzing instrument by means of a pressurized gas. The invention is particularly suited for use in nuclear magnetic resonance (NMR) spectroscopy.

BACKGROUND OF THE INVENTION

Nuclear magnetic resonance spectroscopy has been an important analytical technique since it became available in 1946. When atomic nuclei are placed in a constant, homogeneous, magnetic field of high intensity and subjected at the same time to a radio frequency (RF) field at a selected value, a transfer of energy (resonance) can take place and is measured as a spectral line. Molecules, containing more than one atom, can have nuclei that give rise to many spectral lines depending in part on the type of atom, its location within the molecule, and its interaction with other atomic nuclei within the molecule and with other molecules nearby. This pattern of spectral lines provides physical information about the molecule and its surroundings.

A simple picture is that of the nucleus as a bar magnet. When a system of nuclei is placed within a constant magnetic field, nuclear energy levels are established, corresponding to alignment with and against the applied constant field. A resonance condition can be viewed as a transition between the two energy levels when electromagnetic radiation of a certain frequency $f_o$ is applied to the nucleus. This frequency is referred to as the resonance frequency and is given by the equation:

$$f_o = \gamma H_o / 2\pi$$

where $\gamma$ is a constant known as the gyromagnetic ratio, and is a characteristic of the particular nucleus, and $H_o$ is the magnetic field strength. Therefore, in an NMR spectrometer, spectral characteristics can be measured and used for quantitative and qualitative determinations for the specific nuclei corresponding to the frequency employed.

The breadth of information available by NMR experimentation or analysis is largely due to the fact that nuclei of a given element of interest (e.g., $^1H$ and $^{13}C$) have different resonance frequencies. Moreover, the resonance frequencies of a specific nucleus, such as $^1H$, will vary according to the chemical environment of each nucleus within a molecule. In other words, the resonance frequency of the nuclei of a particular atom of $^{13}C$ will vary depending on how and to whom the atom is bonded. NMR analysis can thus provide qualitative and quantitative information about a molecule and its chemical environment for a particular sample. Within these vague boundaries, NMR spectroscopy can be used for a multitude of purposes including molecular structure determination, tracking the progress of chemical reactions, as well as kinetic and thermodynamic parameters for these processes.

NMR spectroscopy can be used to study chemical systems in liquid, solid or gaseous states. For various reasons, NMR analytical studies are most commonly done using chemical systems in the liquid state, either as analyte(s) dissolved into a particular solvent, or as neat liquids without the addition of solvents or other chemicals.

The apparatus for NMR experiments is relatively simple in concept and comprises a large magnet to create a strong, fixed field, $H_o$ over a defined volume, a number (from about ten to fifty) of smaller direct current (DC) coils (shim coils) with the above defined volume and capable of adjusting the spatial profile of the $H_o$ field, and electronic equipment to generate a RF excitation energy (the transmitter) and to receive a voltage induced into the receiver coil by the system of many nuclei within a sample (the receiver). Often, the coil used to transmit the RF is the same coil as the one that is used for the receiver. The part of the NMR spectrometer in which the sample is placed and where the transmit/receive coil is mounted is known as the probe. While the NMR spectrometer is simple in principle, the manufacture and design are very demanding. This is largely because of the very small signal generated by the resonant nuclei, and because the fixed field must be homogeneous across the sample to within about one part per billion.

A typical magnet used in an NMR spectrometer is of the superconducting variety and is housed in a dewar which includes a room temperature cylindrical bore in which a very carefully controlled homogeneous magnetic field is sustained by operation of the superconducting magnet in the interior of the dewar. The NMR probe for use with a superconducting magnet contains the excitation and detection interface to the sample and is mounted in a cylindrical housing for insertion in the bore.

The principal limitation of NMR as an analytical technique is its low sensitivity, measured as the ratio of the NMR spectral (frequency-domain) signal intensity that is induced into the receiver coil to the noise of the receiver. This measure of sensitivity is often referred to as the signal to noise (S/N) ratio. Improvements in NMR sensitivity have been obtained through advancements in NMR hardware, software and methods. One example is the use of a superconducting solenoid magnet rather than iron magnet for the purpose of generating higher-strength fields. The present invention, however, is primarily concerned with how the different means of sample delivery can affect the sensitivity of the NMR spectrometer.

The signal portion of the signal-to-noise ratio is affected by the number of nuclei in close proximity to the receiver coil (concentration), the filling factor of the RF coil/sample structure (geometry), and the spatial homogeneity of the magnetic field across the sample. For improved sensitivity, it is important that the receiver coil be in close proximity to the nuclei of the sample molecules that are dissolved in the solvent, and that the sample material in the receiver coil is not diluted more than necessary.

The spatial homogeneity of the magnetic field also affects the accurate measurement of spectral lines in samples where the range of intensities of signal resonances is large (large dynamic-range samples). When relatively weak intensity spectral features are located near high-intensity spectral lines, which may be broadened by a less-than-optimal fixed magnetic field homogeneity, the relatively weak intensity spectral features are difficult to observe. This is particularly a problem in situations where solvents are used that have nuclei of the same type (such a $^1H$) as the sample nuclei. In automated chemical analysis, and for the analysis of chemical systems of biological relevance, this situation occurs frequently.

In conventional NMR spectrometers, samples are placed into individual tubes or vials which are then placed into the magnetic field center of the NMR magnetic field volume. Sometimes these samples are spun along their cylindrical axis to improve the resolution of the spectral line. After analysis, the individual tubes are removed from the probe and appropriately disposed. Because of the dynamic handling requirements involved with this type of sample placement, a radial air-gap has typically been located between the outer wall of the sample tube and the inner wall of the probe RF coil structures. Because this air gap results in a less than optimally compact coil structure, the sensitivity of the instrument is necessarily diminished. In particular, the loose coil structure negatively impacts the NMR filling factor. Additionally, the insertion of samples within different sample tubes necessitates frequent adjustment of the currents in the field shim coils, that are placed in or around the probe structure.

Some of the difficulties associated with conventional NMR sample placement has been ameliorated by the development and use of flow-through NMR probes. In a flow-through arrangement, the sample or analyte is conveyed from a sample vessel located outside of the magnetic field volume to the magnetic field center by means of transfer tubing. A portion of the transfer tubing may be a part of the sample delivery system and therefore located external to the NMR spectrometer while a portion of the transfer tubing, referred to herein as internal transfer tubing, is located within the spectrometer. The magnetic field center is that portion of the magnetic field volume having the highest field homogeneity and is therefore the most particularly suited for NMR detection. An NMR flow cell comprising a portion of the internal transfer tubing and composed of an NMR-compatible material is positioned so that its center (i.e., point where detection is designed to occur) is in the magnetic field center of the NMR magnet. Transport of the sample is achieved by injecting it into the magnetic field center using liquid pressure. The liquid may be an additional quantity of sample but more often is a sample-compatible liquid which may be referred to as a solvent, carrier, or means of conveyance. In certain instances, the sample, prior to injection, may have additionally been prepared by dissolution with a particular solvent which may or may not be the same as the carrier solvent. This mobile solvent-phase thus conveys the analyte into and then out of the magnetic field center. The advantages that the flow-through NMR arrangement has over conventional NMR sampling include the elimination of the need for the radial air gap between the sample tube and the RF coil thereby permitting the use of a larger NMR flow cell having a larger internal diameter, a more compact coil structure, minimization of sample handling and removal concerns, and reduction in the need to adjust the field shims from sample to sample. The ability to use a larger NMR flow cell having a larger internal diameter and the ability to have a more compact coil structure significantly improves the S/N ratio and the NMR filling factor.

Although the flow-through NMR sampling using a solvent as a mobile carrier does have advantages over conventional NMR sampling, it is not without its problems. The most notable source or cause of problems is the solvent requirement and the effects this solvent can have on NMR sensitivity and in particular S/N ratio. Potential reduction in the S/N ratio is primarily the result of dilution and contamination. Analyte placed in a solution and conveyed by means of transfer tubes into an NMR spectrometer is no longer located at a definitive position along the length of the transfer tubing. Indeed, diffusion and mixing demand that discrete sources of the analyte will be located throughout the solvent. Therefore any signal detected by the NMR spectrometer will by necessity be diluted. One will also not be able to judge whether any one signal detected for a discrete source of analyte will be representative of the analyte sample as a whole without analyzing the entire solution volume (i.e., there is no guarantee that a homogeneous distribution of the analyte within the solvent exists). Additionally, the solvent is another source of contamination. It can potentially affect the structure of the analyte, thereby changing the resonance frequency associated with the analyte. It can also have a resonance frequency similar to the analyte, thereby masking the analyte's signal. At a minimum, it is a source of noise which can affect the baseline signal.

A better approach, would provide a flow-through NMR arrangement that did not require a liquid solvent as a means of conveyance. Ideally, the means of conveyance would allow the entire analyte to be maintained as a continuous plug in the transfer tubing. Ideally, the means of conveyance would also allow for the positioning of such a plug precisely in the magnetic field center of the magnetic field volume. Such a means of conveyance would have several advantages. Signal strength would be maximized because of the presence of an undiluted analyte in the precise center of the magnetic field center. Additionally, the conveying means would not be a source of contamination or noise. Finally, a better approach would allow for the expedited removal of the analyte sample from the NMR spectrometer after analysis.

SUMMARY OF THE INVENTION

In accordance with one aspect of the invention, there is provided a sample delivery system for flow-through analysis in an NMR spectrometer, the spectrometer having (A) a magnet defining a magnetic field volume and (B) internal transfer tubing for passing a sample through the magnetic field volume and having an inlet end and an outlet end. The sample delivery system comprises a pressure controller having two ends, referred to as an inlet end and an outlet end; a signal processor programmed to control pressure at the outlet end of the pressure controller when a gas pressure is provided at the inlet end of the pressure controller, wherein the pressure is controlled in response to an input signal produced by the NMR spectrometer and detected by the signal processor; a gas transfer tubing having an inlet end and outlet end, with the inlet end of the gas transfer tubing being attached to the outlet end of the pressure controller and with the outlet end being adapted to being inserted into a sample container; and a sample transfer tubing having an inlet end and outlet end with the outlet end of the sample transfer tubing being adapted to being attached to the inlet end of the internal transfer tubing of the NMR spectrometer and the inlet end being adapted to being inserted into a sample container.

In accordance with a second aspect of the invention, there is provided a sample delivery system for flow-through analysis in an NMR spectrometer, the spectrometer having a magnet defining a magnetic field volume and internal transfer tubing for passing a sample through the magnetic field volume and having an inlet end and an outlet end. The sample delivery system comprises a first pressure controller having two ends, referred to as an inlet end and an outlet end; a second pressure controller having two ends, referred to as an inlet end and an outlet end, wherein the outlet end of the second pressure controller is adapted to providing fluid flow into and out of the outlet end of the internal transfer tubing of the NMR spectrometer; a signal processor programmed to control pressure at the outlet end of the first pressure controller when a gas pressure is provided at the inlet end of the first pressure controller and to control pressure at the outlet end of the second pressure controller when a gas pressure is provided at the inlet end of the second pressure controller, wherein the pressures are controlled in response to an input signal produced by the NMR spectrometer or other device along the flow-path and detected by the signal processor; a gas transfer tubing having an inlet end and outlet end, with the inlet end of the gas transfer tubing being attached to the outlet end of the first pressure controller and with the outlet end being adapted to being inserted into a sample container; and a sample transfer tubing having an inlet end and outlet end with the outlet end of the sample transfer tubing being adapted to being attached to the inlet end of the internal transfer tubing of the NMR spectrometer and the inlet end being adapted to being inserted into a sample container.

In accordance with a third aspect of the invention, there is provided a method of achieving precise positioning of a sample and improved signal to noise ratio in flow-through analysis in an NMR spectrometer, comprising a series of operations wherein: a sample is provided; the sample is tapped into; a gas pressure differential is used to transfer the sample into the NMR spectrometer and to position the sample at a desired point relative to a magnetic field; one or more NMR experiments or set of experiments is conducted; and a gas pressure differential is used to force the sample out of the NMR spectrometer.

In accordance with a fourth aspect of the invention, there is provided a program storage device, readable by a signal processor of a sample delivery system for flow-through analysis in an NMR spectrometer and programmed to control pressure at an outlet end of a pressure controller when a gas pressure is provided at an inlet end of the pressure controller, wherein the pressure is controlled in response to an input signal produced by the NMR spectrometer and detected by the signal processor and wherein the gas pressure is used to transport a sample into and out of the NMR spectrometer.

In accordance with a fifth aspect of the invention, there is provided a sample delivery system for flow-through analysis in an NMR spectrometer, the NMR spectrometer having a magnet defining a magnetic field volume and having internal transfer tubing for passing a sample through the magnetic field volume and having an inlet end and an outlet end. The sample delivery system comprises: a pressure controller having two ends, referred to as an inlet end and an outlet end; a signal processor; a program storage device readable by the signal processor and encoding instructions for controlling pressure at the outlet end of the pressure controller when a gas pressure is provided at the inlet end of the pressure controller, wherein the pressure is controlled in response to an input signal produced by the NMR spectrometer and detected by the signal processor; a gas transfer tubing having an inlet end and outlet end, with the inlet end of the gas transfer tubing being attached to the outlet end of the pressure controller and with the outlet end being adapted to being inserted into a sample container; and a sample transfer tubing having an inlet end and outlet end with the outlet end of the sample transfer tubing being adapted to being attached to the inlet end of the internal transfer tubing of the NMR spectrometer and the inlet end being adapted to being inserted into a sample container.

BRIEF DESCRIPTION OF THE DRAWINGS

The foregoing and other advantages of the invention will become apparent upon reading the following detailed description and upon reference to the drawings in which:

FIGS. 3A, 3B, and 3C are three representations of how the volume of sample available will affect the position of the sample within an NMR spectrometer coupled to a sample delivery system of the present invention;

While the invention is susceptible to various modifications and alternative forms, specific embodiments have been shown by way of example in drawings and will be described in detail herein. However, it should be understood that the invention is not intended to be limited to the particular forms disclosed. Rather, the invention is to cover all modifications, equivalents and alternatives falling within the spirit and scope of the invention as defined by the appended claims.

DESCRIPTION OF SPECIFIC EMBODIMENTS

Figure 1:
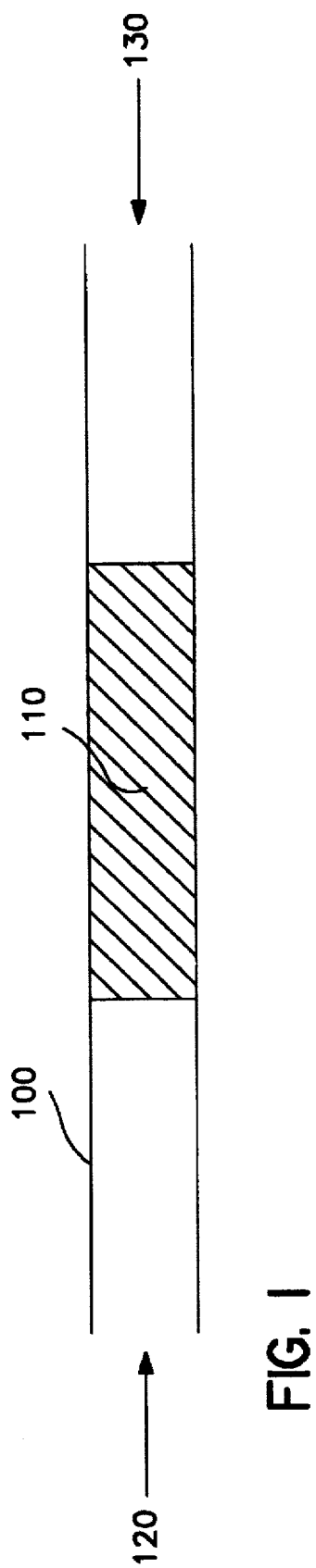
FIG. 1 is a schematic representation of how sample conveyance is achieved according to the invention.

FIG. 1 is a representation of how sample delivery systems of the subsequent embodiments move a sample 110 into and then out of an analytical device attached to the individual sample delivery systems. The sample 110 to be analyzed is located within sample transfer tubing 100. The sample 110 is opposed on one side by forward pressure 120 and on the other side by back pressure 130. The forward pressure 120 and back pressure 130 are provided by gas sources and are controlled by pressure controllers as will be indicated in subsequent descriptions of specific embodiments. Movement of the sample 110 is achieved when a pressure differential exists between forward pressure 120 and back pressure 130. When forward pressure 120 exceeds back pressure 130, the sample 110 moves through the sample transfer tubing 100 in a forward direction (i.e., away from the initial source of sample 110). This situation may be referred to herein as a positive pressure differential condition. Conversely, when back pressure 130 exceeds forward pressure 120, the sample 110 moves through the sample transfer tubing 100 in a backward direction (i.e., toward the initial source of sample 110). This situation may be referred to herein as a negative pressure differential condition.

Figure 2:
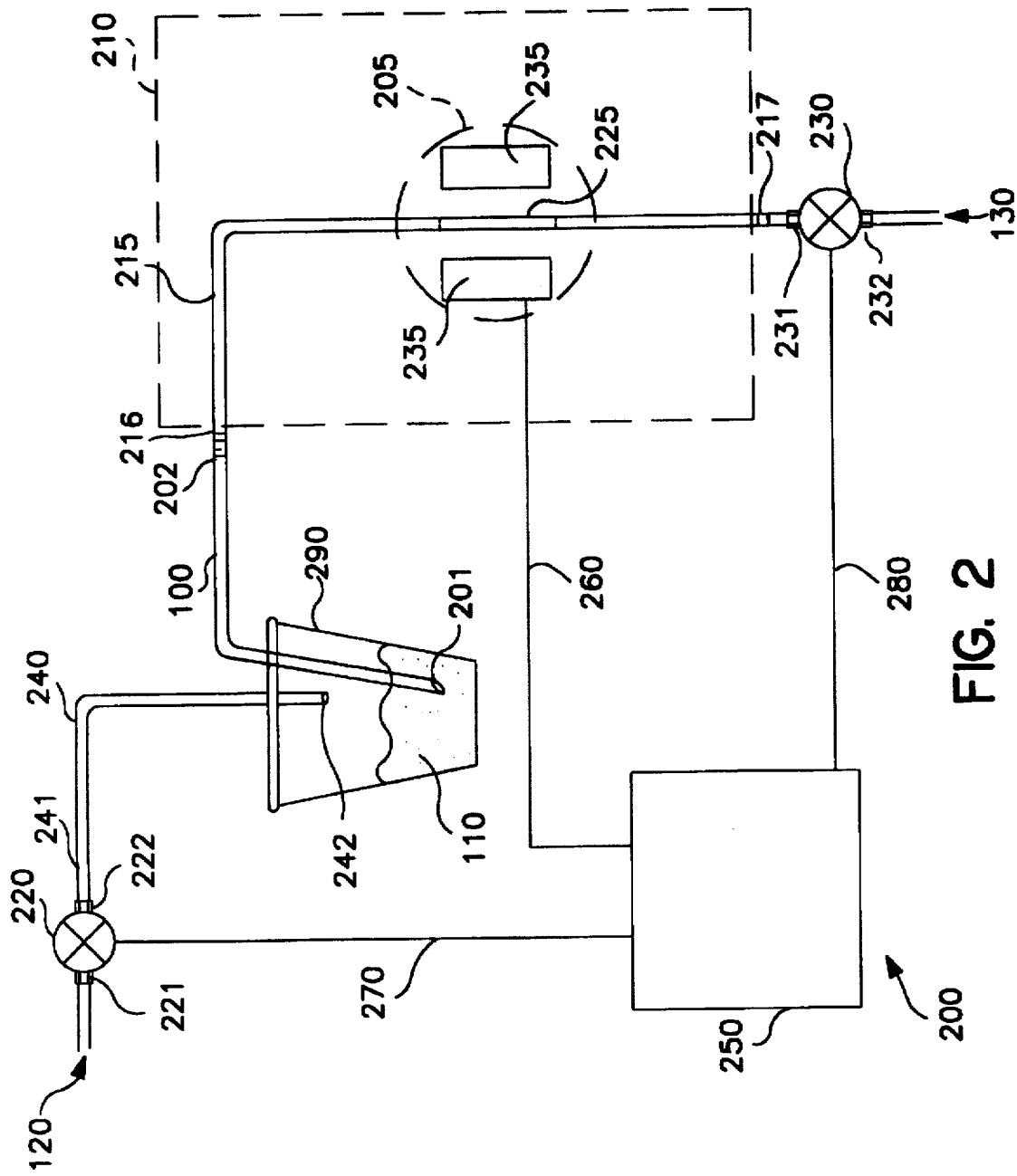
FIG. 2 shows one embodiment of the sample delivery system of the present invention coupled to an NMR spectrometer adapted for flow-through analysis.

FIG. 2 is a representation of an embodiment in which a sample delivery system 200 is coupled to an NMR spectrometer 210 to effectuate the transport of sample 110 into and subsequently out of the NMR spectrometer 210. The sample delivery system 200 is comprised of a first pressure controller 220 having an inlet end 221 and outlet end 222, a second pressure controller 230 having an outlet end 231 and inlet end 232, gas transfer tubing 240 having an inlet end 241 and outlet end 242, sample transfer tubing 100 having an inlet end 201 and outlet end 202, a signal processor 250, a signal input line 260, a first signal output line 270, and a second signal output line 280. A sample container 290 is also indicated. The sample container 290 will not necessarily constitute an element of the sample delivery system 200; however, a sample container 290 capable of maintaining an applied pressure is integral to the functioning of the sample delivery device 200. In other words, it is not necessary for the sample container 290 to be permanently fixed in the position indicated. Indeed it is expected that in other embodiments a sample tray containing numerous sample containers 290 could be adapted for use with the sample delivery system 200. Sample trays of this sort are used in the field for other analytical devices, and it is expected that the sample delivery system 200 could be similarly adapted by means known to those of ordinary skill in the art. In various embodiments the individual sample containers 290 could be moved so as to position them in contact with the gas transfer tubing 240 and sample transfer tubing 100, or, alternately the gas transfer tubing 240 and sample transfer tubing 100 could be moved to position them in contact with an individual sample container 290 located on a sample tray.

In this embodiment indicated in FIG. 2, the NMR spectrometer 210, is an NMR spectrometer adapted for flow-through analysis. The NMR spectrometer 210, to which the sample delivery system 200 is coupled, is characterized by an analysis zone 205 and internal transfer tubing 215 having an inlet end 216 and outlet end 217. Inlet end 216 and outlet end 217 of the internal transfer tubing 215 are thus the inlet and outlet of the NMR spectrometer 210. The analysis zone 205 is further characterized by a NMR flow cell 225 which comprises a portion of the internal transfer tubing 215, and magnet 235 which is capable of producing a magnetic field. The internal transfer tubing 215 passes through the magnet 235. This magnet 235 may be a permanent magnet, non-superconducting electromagnet, superconducting magnet, or any other magnet of the kind well-known in the art or subsequently developed. The NMR flow cell 225 is located within the magnet 235 and is optimally aligned with the magnetic field center so as to expose the greatest volume of sample possible to the magnetic field center. The portion of the internal transfer tubing 215 comprising the NMR flow cell 225 may have an internal diameter that exceeds the internal diameter of the remaining portions of the internal transfer tubing. As previously indicated, this increased internal diameter allows for increased NMR sensitivity by increasing both the NMR S/N ratio and the NMR filling factor.

The sample transfer tubing 100 and internal transfer tubing 215, including that portion of the internal transfer tubing 215 comprising the NMR flow cell 225, may be collectively referred to herein as "transfer tubing".

A gas source capable of providing a forward pressure 120 is coupled to the inlet end 221 of the first pressure controller 220. The outlet end 222 of the first pressure controller 220 is attached to the inlet end 241 of the gas transfer tubing 240. The outlet end 242 of the gas transfer tubing 240 and the inlet end 201 of the sample transfer tubing 100 are inserted into the sample container 290. The inlet end 201 of the sample transfer tubing 100 should be preferably positioned within the sample container 290 in a manner to allow for the transfer of a substantial portion of the sample 110 located within the sample container 290. The outlet end 242 of the gas transfer tubing 240 is preferably placed at a position above any expected sample level. By maintaining outlet end 242 of the gas transfer tubing 240 in such a position (i.e., above the sample level), the possibility of significant admixing (either by true mixing or by diffusion) of the sample 110 and gas providing the forward pressure 120 should be at a minimum.

The outlet end 202 of the sample transfer tubing 100 is coupled to the inlet end 216 of the internal transfer tubing 215. The outlet end 217 of the internal transfer tubing 215 is coupled to the outlet end 231 of the second pressure controller 230. A second gas source capable of providing a back pressure 130 is coupled to the inlet end 232 of the second pressure controller 230.

Signal processor 250 receives signals from the NMR spectrometer 210 via signal input line 260. Signal processor 250 transmits signals (based on signals received from the NMR spectrometer) to the first pressure controller 220 via the first signal output line 270 and to the second pressure controller 230 via the second signal output line 280. The output signals transmitted from the signal processor 250 cause the pressure controllers 220 and 230 to adjust the forward pressure 120 and back pressure 130 passing through the pressure controllers 220 and 230.

Once the sample container 290 containing the sample 110 has been positioned as indicated but prior to the commencement of NMR analysis, the forward pressure 120 and back pressure 130 are equal. Forward conveyance or transfer of the sample 110 into the transfer tubing and eventually into the analysis zone 205 is initiated by adjusting the pressure differential between the forward pressure 120 and back pressure 130 so that the forward pressure 120 exceeds the back pressure 130 (i.e., positive pressure differential condition). Preferably, this is achieved by raising the forward pressure 120 while maintaining the back pressure 130 at a constant level. Optionally, the positive pressure differential condition can be achieved by lowering the back pressure 130 while either increasing the forward pressure 120 or maintaining it at a constant level.

The gas chosen as the conveying means should be unreactive with any sample 110. It is not an absolute requirement that the gas source for the forward pressure 120 and back pressure 130 be the same, although convenience would suggest that the same gas be used for both. The preferred gas is nitrogen, also referred to as dry nitrogen or "high purity nitrogen".

The gas pressure applied in either direction (i.e., forward pressure 120 and back pressure 130) should be sufficient to convey the sample through the entire length of transfer tubing in a timely manner. Gas pressures, however, should not be so high as to cause the gas to break up the continuity of the sample 110 as it passes through the transfer tubing (i.e., the sample should exist as a continuous sample plug). Preferably, gas pressures should be low enough that even diffusion of the gas into the sample plug does not occur to a significant degree. Maximum continuity of the sample 110 is desired because of the beneficial effect that this condition has on NMR sensitivity as indicated by signal to noise (S/N) ratio. In conventional NMR spectrometers adopted for flow-through analysis, signal strength is negatively impacted by the need to use a liquid solvent as the conveying means. Mixing of the sample 110 within the solvent carrier and diffusion of the sample 110 into the solvent carrier causes the individual sample entities to be located throughout the solvent carrier. The obvious result of this mixing and diffusion is that the concentration of the sample 110 within the carrier and passing through the transfer tubing exists as a gradient. The signals generated by the sample 110 as it passes through the NMR flow cell 225 and magnetic field will therefore vary according to this gradient. Any determination of the true signal strength must take into account this dilution. Additionally, the presence of a solvent carrier negatively impacts the S/N ratio because it is a potential source of noise. The carrier will typically have a signal associated with it which must be subtracted or otherwise accounted for. Additionally, the solvent may contain contaminants which will be an additional source of noise. Also, the concentration gradient can affect field homogeneity, resulting in increased setup time and potentially affecting the shape of the spectral lines and the S/N ratio.

By using pressurized gas as the conveying means, many of the undesirable effects of a solvent earlier can be avoided. Because mixing and diffusion do not occur to a measurable degree, the sample 110 is not diluted (i.e., the sample 110 is maintained as a plug). The signal strength generated by a specific structure will only vary if the concentration of this species varies within the sample 110. Because total analysis volume will be less when a solvent is not used, it should be expected that any concentration variations, and therefore signal variations, should be substantially less when gas conveyance rather that solvent conveyance is used. Additionally, because admixture of the carrier gas and sample does not occur to any significant degree, any additional source of noise which might be associated with the carrier can be avoided by ensuring that only the sample 110 occupies that portion of the transfer tubing and specifically that portion of the NMR flow cell being subjected to NMR analysis (i.e., the magnetic field center). Precise positioning of the sample in the manner described can be achieved with the sample delivery system 200 by the method subsequently described.

As sample transfer commences, due to the positive pressure differential condition, NMR detection is initiated. NMR signals are monitored by the signal processor 250. Monitoring of the NMR signals may employ digital or analog feedback techniques as known to those of ordinary skill in the art. When a strong consistent signal is detected, the signal processor 250 causes the adjustment of either the forward pressure 120 (i.e., by means of the first pressure controller 220), the back pressure 130 (i.e., by means of the second pressure controller 230), or some combination of the two to obtain a pressure differential of zero. When the pressure differential is zero, movement of the sample 110 ceases. Precise positioning of the sample 110 within the desired region is preferably achieved by employing minimal pressures to effectuate movement and by gradually slowing movement of the sample 110 when its presence in the approximately desired position is detected (i.e., slowly adjusting the pressure differential once an initial increase in signal strength is detected). Using these preferred methods, it should be possible to position that portion of the sample 110 having the highest S/N ratio precisely within the magnetic field center.

Once desired positioning of the sample 110 and a zero or near-zero pressure differential are achieved, the NMR experiment can be conducted. It is preferred that a zero pressure differential and therefore cessation of movement of the sample 110 be achieved prior to the commencement of the NMR experiment, but the NMR experiment can be conducted in a situation in which the sample is moving. When the signal processor 250 detects via signal input line 260 that the NMR experiment has been concluded, the sample is flushed (i.e., removed) from the NMR spectrometer 210. In the present embodiment, removal of the sample is achieved by withdrawing it back into the sample container 290. Removal of the sample 110 from the NMR spectrometer 210 is achieved by adjusting the pressure differential so that the back pressure 130 exceeds the forward pressure 120 (i.e., negative pressure differential condition). Obviously, to minimize the amount of time required for each analysis, it would be desirable to know precisely when all of the sample 110 had been returned to the sample container 290. One way to minimize the time allocated for removal is to take a log of the flow rate versus time for the initial introduction of the sample 110. The data taken from this log can then be used to determine what combination of flow rate and time will be necessary to purge the NMR spectrometer 210 of sample 110. The flow rate and time data can be collected by means known to those of ordinary skill in the art and then used by the signal processor 250 to adjust the pressure differential. It is expected that other means known to those of ordinary skill in the art could also be used. These might include monitoring for a drop in signal strength and establishing a set time period commencing with this drop in signal strength that would guarantee complete removal of the sample 110.

It should be evident from FIG. 2 that the gas providing the forward pressure 120 and back pressure 130 are, like the sample 110, mobile phases. The volume of gas opposing the sample 110 as a forward pressure 120 and back pressure 130 will necessarily vary depending upon the direction of movement of the sample 110 within the transfer tubing. Therefore, a means must be provided for handling the gas passing back through the outlet ends 222 and 231 of the first and second pressure controllers 220 and 230. Any of the means known to those of ordinary skill in the art may be employed. If the gas sources of forward pressure 120 and back pressure 130 are discrete finite sources such as individual cylinders, or cylinder, the removal of the conveying gas is easily achieved by simply forcing the gas back into the cylinders. If, however, the gas sources are dedicated plant gas lines, this solution will probably not be available. In that instance four-way pressure controllers could be used for the first pressure controller 220 and second pressure controller 230 to allow the nitrogen or other conveying gas to be vented from the sample delivery system 200. From this description, those of ordinary skill will of course recognize that the removal of excess conveying gas can be accomplished by any number of means.

It should also be evident from FIG. 2 that depending on the volume of sample 110 initially in sample container 290, the position of the interface between the sample and the gas providing the forward pressure 120 will vary. When the forward pressure 120 and back pressure 130 have been equalized and the sample 110 has been precisely positioned in the magnetic field center, this interface may exist within the sample container 290, the sample transfer tubing 100, or the internal transfer tubing 215. However, the volume of sample 110 in the sample container 290 should, for maximum NMR sensitivity, always be sufficient to completely occupy the portion of the analysis zone 205 comprising the magnetic field center (i.e., no nitrogen in the magnetic field center) and preferably, should be sufficient to completely occupy the NMR flow cell 225. Three potential interfaces, two desirable for optimal NMR sensitivity and one undesirable for optimal NMR sensitivity, are shown in FIG. 3. In FIG. 3A, the initial volume of sample 110 present is sufficient to allow the interface 300 between the sample 110 and gas providing the forward pressure 120 to remain in the sample container 290 and to allow the sample 110 to completely occupy the analysis zone 205 of the NMR spectrometer. In FIG. 3B, the initial volume of sample 110 present is sufficient to allow the sample 110 to completely occupy the analysis zone 205 of the NMR spectrometer 210, but is not sufficient to allow the interface 300 between the sample 110 and gas providing the forward pressure 120 to remain in the sample container 290. The interface 300 may exist in the sample transfer tubing 100 or the internal transfer tubing 215. The conditions depicted in FIGS. 3A are 3B are mutually acceptable for optimal NMR sensitivity. If however, as indicated in FIG. 3C, the initial volume of sample 110 is insufficient to completely occupy the analysis zone 205 of the NMR spectrometer 210, NMR sensitivity and spectral resolution may suffer.

In other embodiments, it may be desirable to more completely ensure that the transfer tubing is completely devoid of sample 110 or other residual matter. A cleaning operation is typically used to achieve these ends. Any of the widely known cleaning protocols can be used with the sample delivery system 200/NMR spectrometer 210 combination. Optionally, a cleaning protocol specifically devised for a new application or analysis can be employed. One known cleaning protocol that can be employed calls for successive washes of a aqueous acid, such as hydrochloric acid (HCl), and acetone. Those of ordinary skill will of course recognize that the sample delivery system 200 may include other conventional components to permit flushing (i.e., cleaning) out the system between samples 110 to avoid cross-contamination. For example, the sample transfer tubing 100 may include one or more ports, valves, tees, etc., for introducing cleaning solutions (e.g., HCl and acetone) or flushing gas (e.g., dry nitrogen). Flushing of these cleaning agents through the transfer tubing can be achieved by placing the agents in sample containers 290 and then by varying the pressure differential across the transfer tubing in the way previously described. The cleaning agents can be passed through the transfer tubing any number of times. The cleaning operation is preferably concluded by flushing the transfer tubing with nitrogen. This can be achieved by any number of means, two of which are: coupling an empty sample container 290 to the sample delivery system 200 and incorporating a bypass from the first pressure controller 220 to the sample transfer tubing 100 thereby allowing nitrogen to pass into the transfer tubing (i.e., both sample transfer tubing 100 and internal transfer tubing 215) without having to pass through a sample container 290. Nitrogen, for the purposes of purging, can also be provided from the second pressure controller 230, passed through the transfer tubing, and then through either the bypass or an empty sample container. The nitrogen by any of these methods can then be removed from the system by any of the methods previously described, including venting the nitrogen from a port on one of the pressure controllers 220 and 230, or passing the nitrogen back into a nitrogen cylinder.

Figure 4:
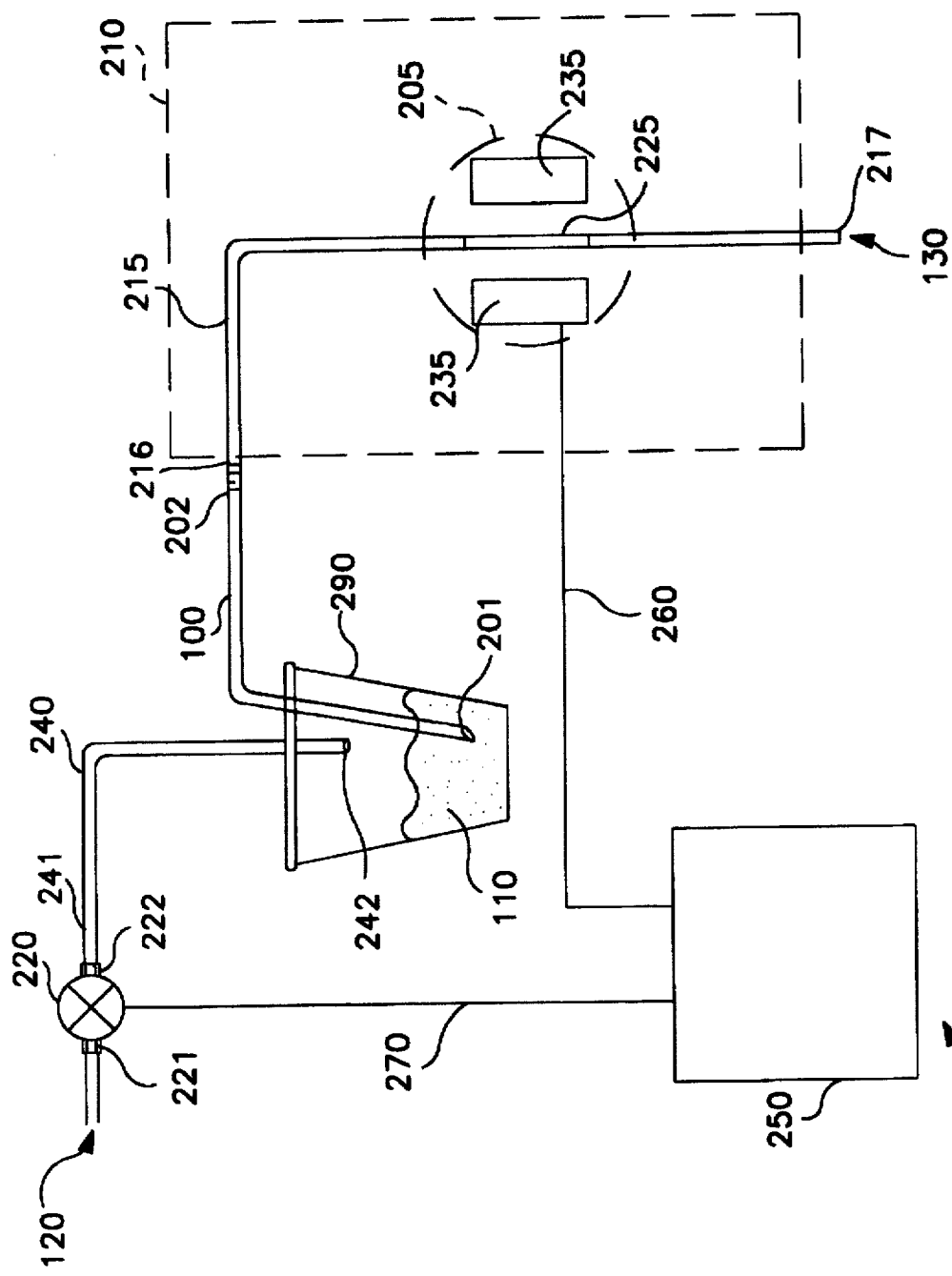
FIG. 4 shows a second embodiment of the sample delivery system of the present invention coupled to an NMR spectrometer adapted for flow-through analysis.

In another embodiment the back pressure 130 can be provided by atmospheric pressure. This method is viable because, as previously indicated, one of the preferred ways to achieve conveyance of a sample 110 is to raise and lower the forward pressure 120 while maintaining the back pressure 130 constant. In this embodiment, the constant back pressure 130 is atmospheric pressure. Use of this embodiment will obviate the need for the second pressure controller 230. A pressure differential of zero, hence no sample movement, is obtained by adjusting the forward pressure 120 to be equal to atmospheric pressure. Forward conveyance (i.e., positive pressure differential condition) is achieved by increasing the forward pressure 120 relative to atmospheric pressure, and negative or backward conveyance (i.e., negative pressure differential condition) is achieved by decreasing the forward pressure 120 relative to atmospheric pressure. Although this embodiment is viable, it is not preferred because of the potential reactivity of oxygen and other elements in the atmosphere with the sample 110. Additionally, because of the minimal pressures and pressure differentials required to achieve sample conveyance, minor variations in atmospheric pressure could have significant detrimental effects on sample analysis. This embodiment is indicated in FIG. 4.

Figure 5:
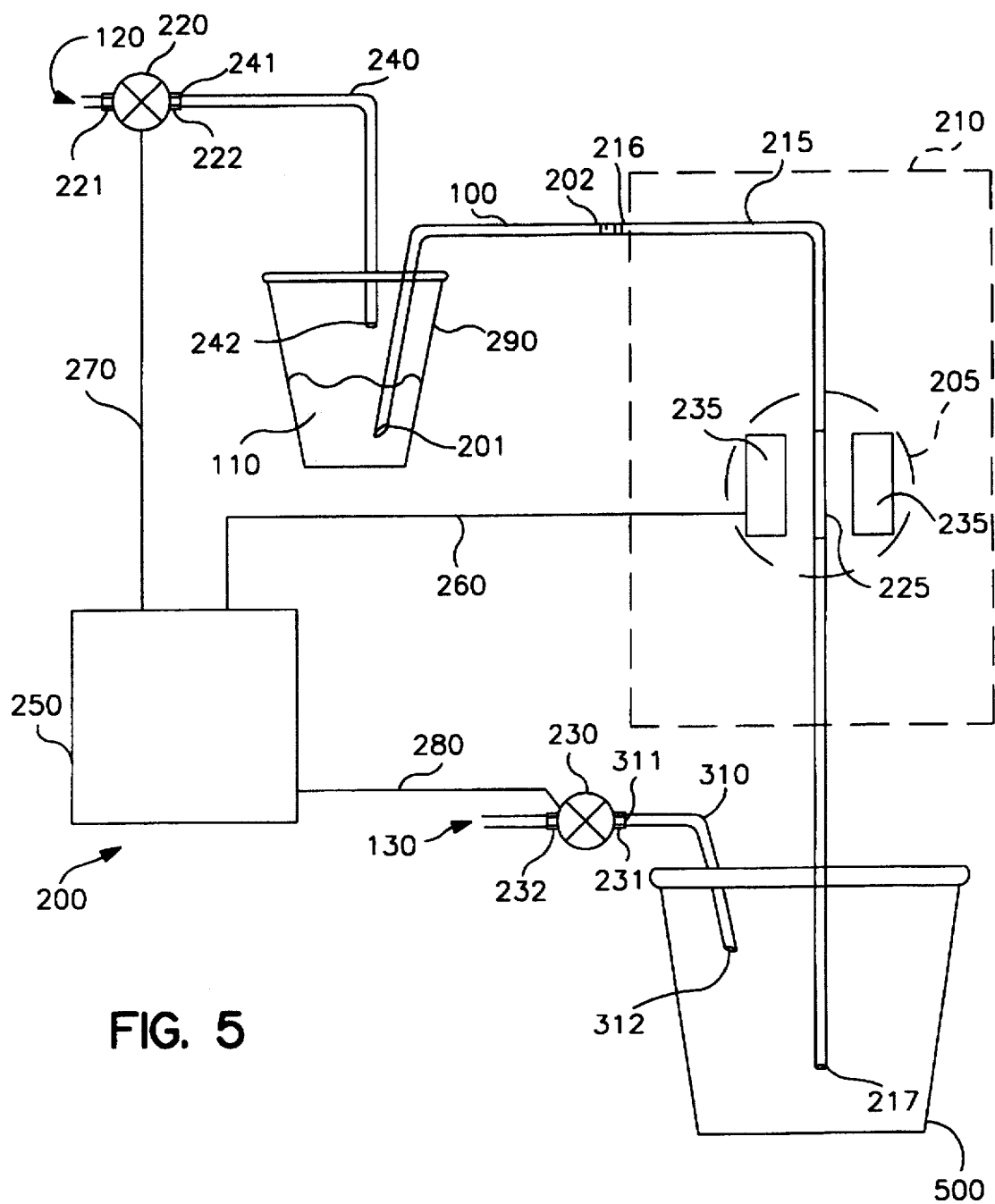
FIG. 5 shows a third embodiment of the sample delivery system of the present invention coupled to an NMR spectrometer adapted for flow-through analysis.

In another embodiment, indicated in FIG. 5, a collection container 500 is placed at the outlet end 217 of the internal transfer tubing 215. Like the sample container 290, the collection container 500 is capable of maintaining a pressure applied to it. The purpose of the collection container 500 is to collect analyzed samples 110 when it is not desired to return them to the sample container 290. The volumetric capacity of the collection container 500 should at least be sufficient to hold the maximum expected volume of sample 110 and to allow for a small headspace above the collected sample 110. Preferably, the collection container 500 has sufficient volumetric capacity to hold numerous analyzed samples 110. This situation is preferred in order to minimize the need to constantly empty the collection container 500.

A second gas transfer tubing 310, having an inlet end 311 and outlet end 312 is also depicted in FIG. 5. The outlet end 312 of the second gas transfer tubing is inserted into the collection container 500. The outlet end 231 of the second pressure controller 230 is attached to the inlet end 311 of the second gas transfer tubing 310. A source of gas providing back pressure 130 is thus attached to the inlet end 232 of the second pressure controller 230. Conveyance of an analyzed sample 110 to the collection container 500 is achieved by the following steps. Once the signal processor 250 detects that the NMR experiment has concluded, signals are sent to the two pressure controllers 220 and 230 via signal output lines 270 and 280. These signals cause the pressure controllers 220 and 230 to adjust the forward pressure 120 and back pressure 130 to achieve a positive pressure differential condition (i.e., a condition in which the forward pressure 120 exceeds the back pressure 130). The pressure differential causes the sample 110 to pass out of the NMR spectrometer 210 and into the collection container 500. The complete absence of the sample 110 from the transfer tubing can be determined by any of the means previously described or by any means known to those skilled in the art. These might include logging flow rate, time, and total length of transfer tubing to determine a desired purging period or having the signal processor 250 detect a pressure drop at the pressure controllers 220 and 230 that will occur when all of the sample 110 is located in the collection container 500.

In a variation of the embodiment depicted in FIG. 5, it may be desirable to replace the collection container 500 with a second analytical instrument, such as a high pressure liquid chromatograph (HPLC) or any liquid separation technique, UV-VIS spectrophotometer, mass spectrometer, or perhaps another NMR spectrometer. The second analytical instrument might alternatively be placed after the collection container 500, in which case it will be necessary to have tubing connecting the second analytical instrument to the collection container 500. The measurement (signal output) from the first NMR spectrometer 210 (or device) could be analyzed automatically and a logical decision made on how to route the sample. The logical decision could be made by the operator or by a signal processor programmed to make the selection based upon input provided. One ordinarily skilled in the art should recognize that it may be possible to have several instruments after the initial instrument, either in series or parallel, that can conduct further analyses based on the results of the first instrument or some other protocol. It should also be evident that the sample delivery system 200/NMR spectrometer 210 combination indicated in FIG. 5 might not be the first analytical instrument in such an analysis chain and that any of the previously indicated analytical techniques or others may precede the sample delivery system 200/NMR spectrometer 210 combination. If this were the case, it would be necessary to adapt the sample container 290 employed with the sample delivery system 200/NMR spectrometer 210 combination so as to accept sample 110 from an upstream instrument. One such example of how instruments could be coupled in an analysis chain might be the use of a lower field NMR spectrometer that has an associated analysis cost as an initial screening tool to determine whether a sample 110 needed to be sent to either an additional NMR analysis that might be conducted by a higher field NMR spectrometer having a considerably higher associated analysis cost or alternatively to some other analytical instrument or a drain.

In another embodiment it may again be desirable to conduct a cleaning operation after experimentation employing the embodiment depicted in FIG. 5 is employed. Any of the previously described cleaning operation can again be employed.

Figure 6:
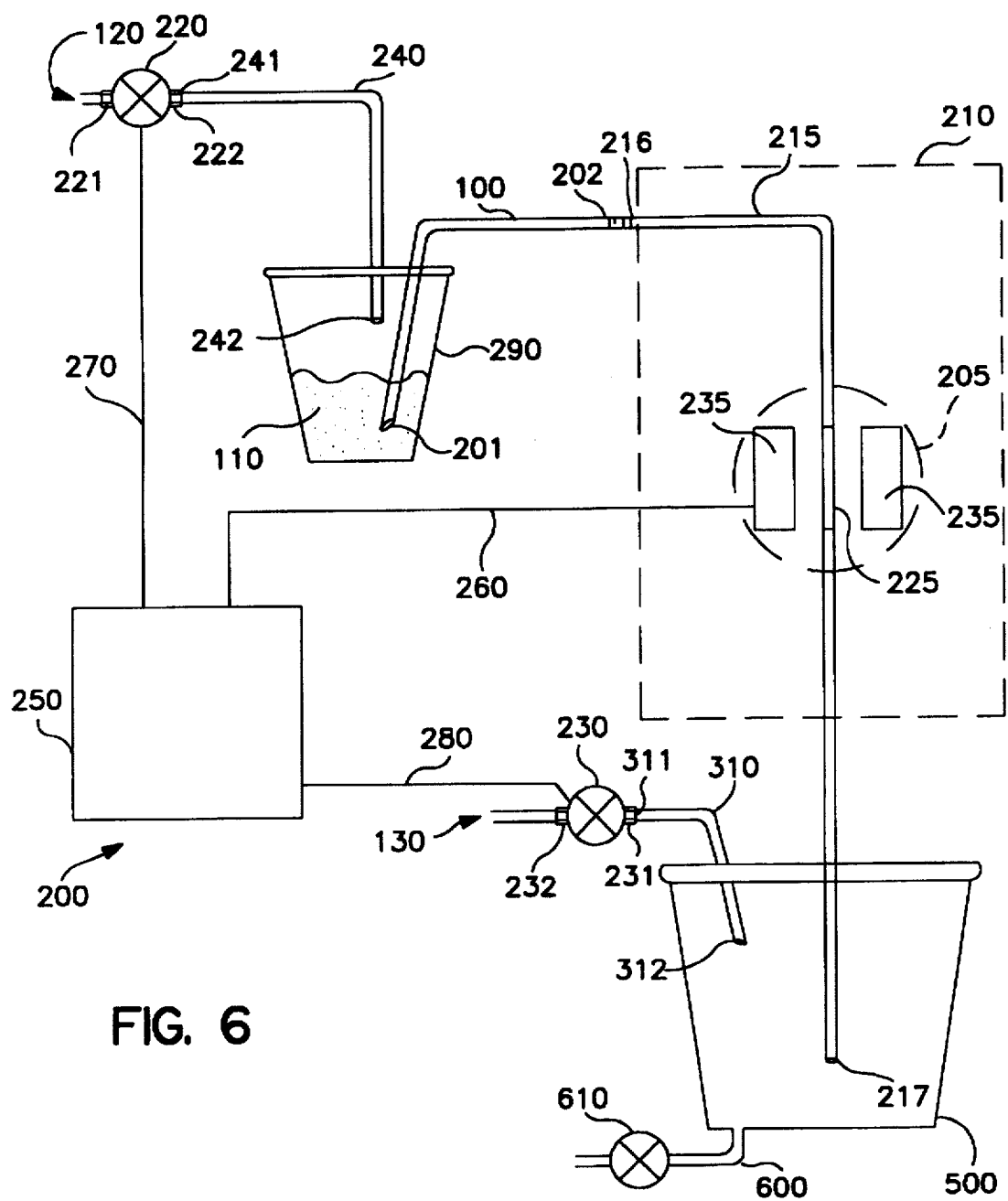
FIG. 6 shows a fourth embodiment of the sample delivery system of the present invention coupled to an NMR spectrometer adapted for flow-through analysis.

In another embodiment, depicted in FIG. 6, it may be desirable to continuously or periodically withdraw analyzed sample from the collection container without physically decoupling the collection container 250 from the sample delivery system 200. One way in which this can be achieved is to provide a drain line 600 having a control valve 610 that can be opened to permit removal of the analyzed sample 110. In order to maintain pressure during sample delivery and analysis, the draining operation should only be conducted when experimentation or analysis is completed. This operation can be accomplished by using automatic or manual valves in ways known to those of ordinary skill in the art. Pressure differential as previously described can be used to effectuate the removal of the sample from the collection container 500 via the drain line 600. In a variation of this embodiment, the drain 600 might be connected to a downstream analytical instrument as previously described.

Figure 7:
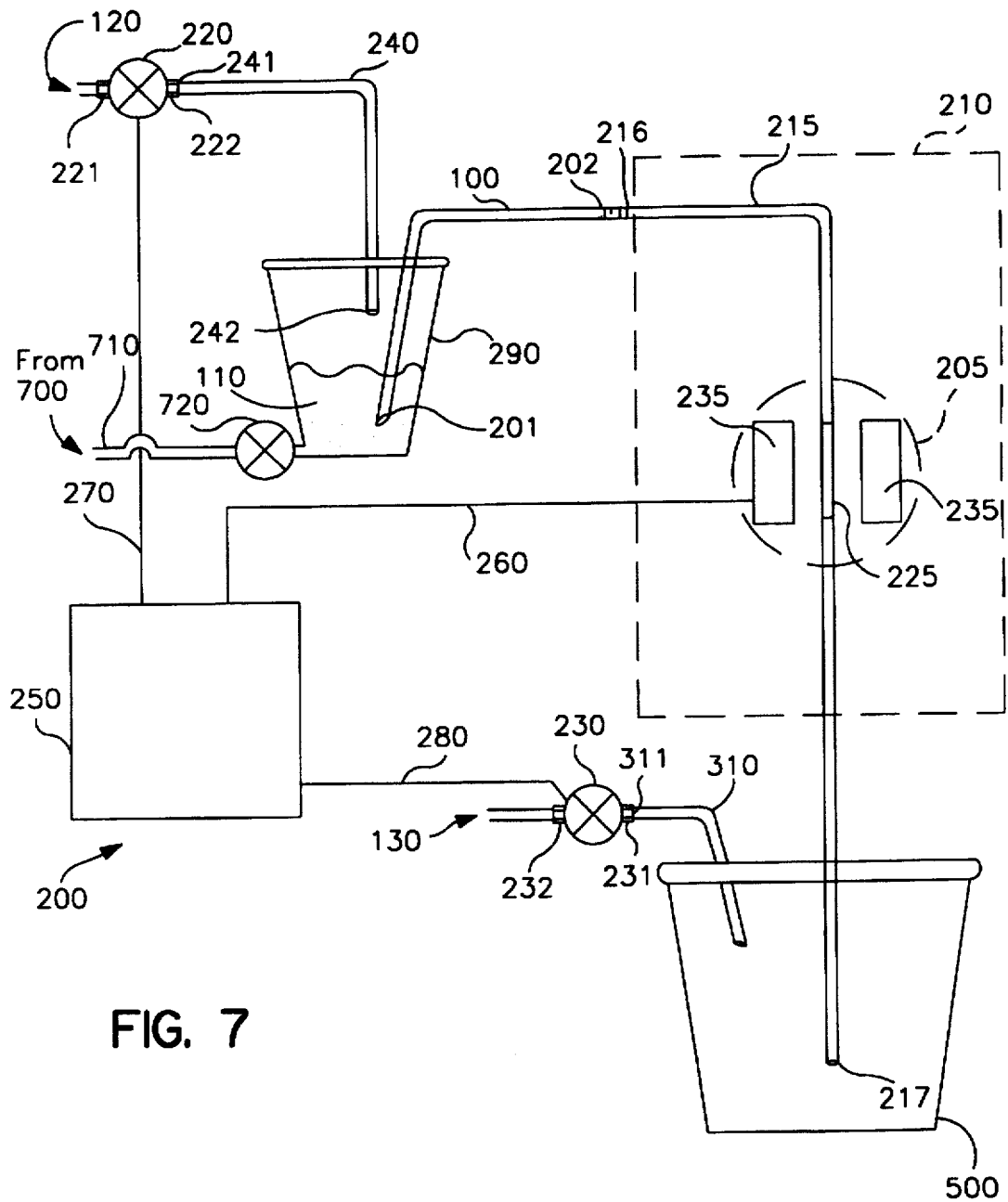
FIG. 7 shows a fifth embodiment of the sample delivery system of the present invention coupled to an NMR spectrometer adapted for flow-through analysis.

In another embodiment, depicted in FIG. 7, it may be similarly desirable to have a means to continually or periodically provide sample 110 to the sample container 290. This in particular would be desirable when the NMR spectrometer 210 is being used as an on-line quality control method for a chemical process. The sample delivery system 200/NMR spectrometer 210 combination could be coupled to a process 700 via product sample tubing 710 having a control valve 720. By this combination, the supply of sample 110 in sample container 290 could be continually or periodically refreshed whenever analysis was desired. Again, in order to maintain pressure during sample delivery and analysis, the supply of sample 110 should only be refreshed after analysis is complete. This operation can be accomplished by using automatic or manual valves in ways known to those of ordinary skill in the art. In a variation of this embodiment, the process 700 might be replaced by an upstream analytical instrument as previously described.

In another embodiment it may be desirable or even necessary to dilute the sample 110 with an appropriate solvent. Although the presence of the solvent is not necessary as a conveying means, it may at times be necessary to dilute the sample 110 with an appropriate solvent. Two instances where dilution might be appropriate is where the sample volume available is insufficient to completely fill that portion of the NMR flow cell 225 aligned with the magnetic field center and where the signal obtained from the sample 110 is too strong. The appropriate solvent for a particular sample 110 will vary as known to those of ordinary skill in the art depending on the composition of the sample 110. Under conditions such as these, where the presence of a small quantity of solvent is desirable, use of the described sample delivery systems 200 should still provide improved NMR sensitivity over sample delivery systems employing a solvent as a means of conveyance (i.e., carrier).

Figure 8:
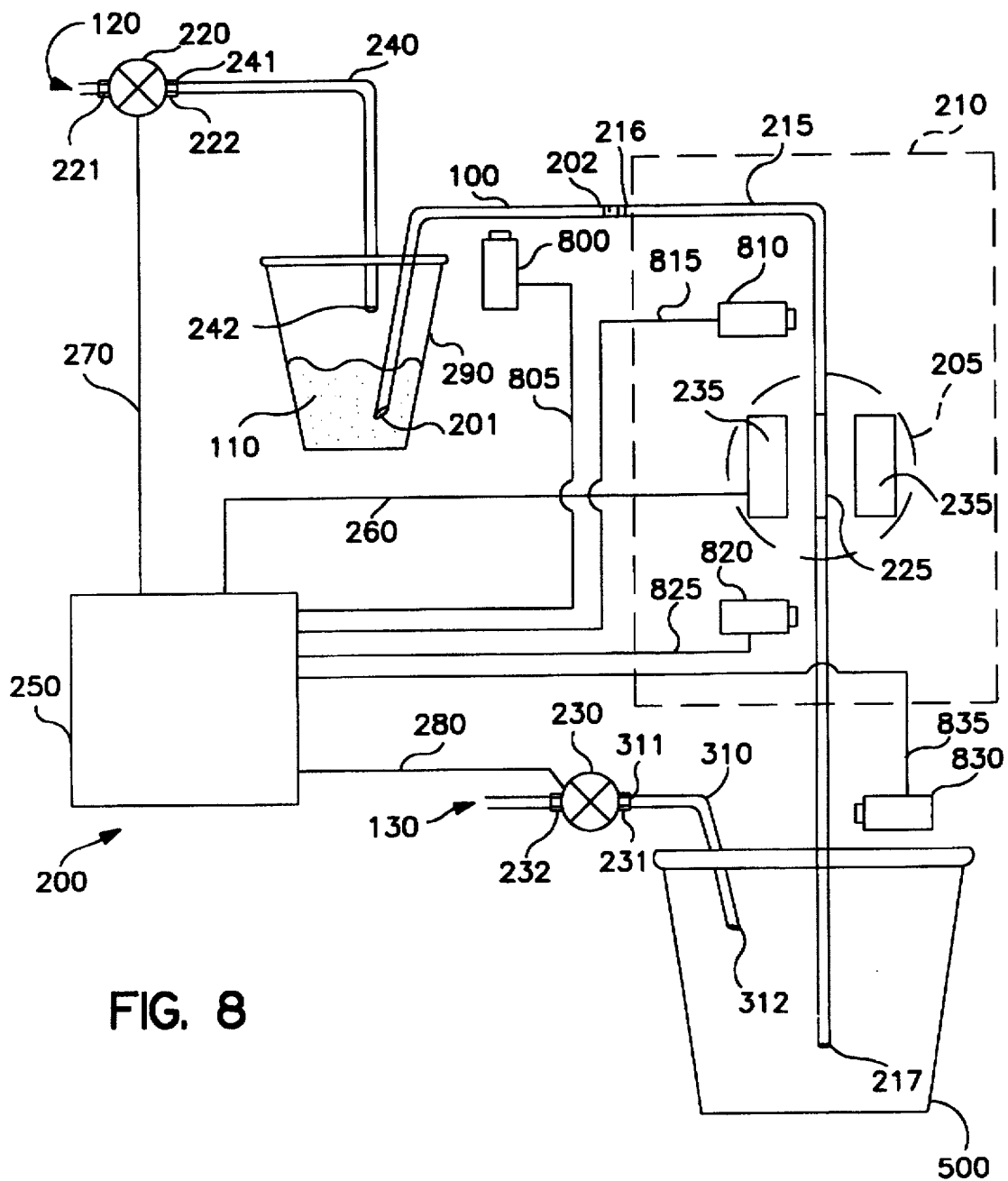
FIG. 8 shows an eighth embodiment of the sample delivery system of the present invention coupled to an NMR spectrometer adapted for flow-through analysis.

In other embodiments, it may be desirable to place other detectors, such as UV detectors, along the transfer tubing so as to effectuate either the precise positioning of the sample 110 in the magnetic field center or the complete removal of the sample 110 from the transfer tubing once the NMR experiment has been conducted. Depending upon their position relative to the other components in the sample delivery system 200/NMR spectrometer 210 combination, the detectors may be more suited to effectuating the precise positioning of the sample 110 within the magnetic field center or the complete removal of the sample 110 from the transfer tubing (e.g., either returning the sample 110 to the sample container 290 or conveying the sample 110 to the collection container 500). The signals from the detectors are sent to the signal processor 250 by signal input lines. The signals, at a minimum, indicate the presence or absence of sample 110 at that point of the transfer tubing observed by the individual detectors. The signal processor 250 then uses these signals, possibly and preferably in combination with the signals obtained from the NMR spectrometer 210 via signal input line 260, to determine how the forward pressure 120 and back pressure 130 flowing through pressure controllers 220 and 230 should be adjusted to achieve the desired purpose (i.e. precise positioning of the sample 110 or complete removal of the sample 110). Detector or detectors positioned closer to the magnetic field center of the NMR magnet (i.e., the farther they are to the magnet 235) are more particularly suited for effectuating precise positioning of the sample 110. Detector or detectors positioned further away from the magnetic field center of the NMR magnet (i.e., the closer they are to the magnet 235) are more particularly suited for effectuating the complete removal of the sample 110. In certain embodiments, such as that depicted in FIG. 8, it may be desirable to position multiple UV detectors along the transfer tubing to achieve both purposes. In FIG. 8, four UV detectors 800, 810, 820, and 830 are positioned at different point along the transfer tubing. Two of the detectors 800 and 810 are positioned prior to the NMR flow cell 225, and two of the detectors 820 and 830 are positioned after the NMR flow cell 225. The detectors 800, 810, 820, and 830 transmit signals to the signal processor 250 via signal input lines 805, 815, 825, and 835. The detectors 800 and 830 positioned at the greatest distance from the NMR flow cell 225 are better suited for effectuating the removal of sample 110, whereas the two detectors 810 and 820 positioned closer to the NMR flow cell 225 are better suited for effectuating the precise positioning of the sample 110 for NMR experimentation. Those of ordinary skill will of course recognize that the detector type chosen, the number of detectors, and the position of the detectors along the transfer tubing may vary significantly depending upon the precision of sample 110 positioning desired or the degree to which the operator wishes to be assured that the sample 110 has been completely removed from the transfer tubing.

It will be apparent to those of ordinary skill having the benefit of this disclosure that the signal processor 250 may be any device or entity capable of receiving input signals, formulating response actions to these input signals, and communicating these formulated responses by output signals. In its least automated but operable form, the signal processor's function could be performed by a human operator who would observe the signals generated by the NMR spectrometer 210 or other instrument and then formulate the appropriate response (i.e., appropriate changes in pressure) to the signals. In other embodiments, the signal processor 250 can be any combination of electronic software or hardware programmed to accomplish these actions. Indeed, any of the foregoing variations may be implemented by programming a suitable general-purpose computer having appropriate hardware. The programming may be accomplished through the use of a program storage device readable by the computer and encoding a program of instructions executable by the computer for performing the operations described above. The program storage device may take the form of, for example, one or more floppy disks; a CD ROM or other optical disk; a magnetic tape; a read-only memory chip (ROM); and other forms of the kind well-known in the art or subsequently developed. The program of instructions may be "object code," i.e., in binary form that is executable more-or-less directly by the computer; in "source code" that requires compilation or interpretation before execution; or in some intermediate form such as partially compiled code. The precise forms of the program storage device and of the encoding of instructions is immaterial here.

It will be appreciated by those of ordinary skill having the benefit of this disclosure that numerous variations may be possible without departing from the spirit and scope of the invention defined by the appended claims.

What is claimed is:

1. A fluid sample delivery system for flow-through analysis in an NMR spectrometer, the spectrometer having (A) a magnet defining a magnetic field volume and (B) internal transfer tubing for passing a sample through the magnetic field volume and having an inlet end and an outlet end, the sample delivery system comprising:

(a) a pressure controller having two ends, referred to as an inlet end and an outlet end;

(b) a signal processor programmed to control pressure at the outlet end of the pressure controller when a gas pressure is provided at the inlet end of the pressure controller, wherein the pressure is controlled in response to an input signal produced by the NMR spectrometer and detected by the signal processor;

(c) a gas transfer tubing having an inlet end and outlet end, with the inlet end of the gas transfer tubing being attached to the outlet end of the pressure controller and with the outlet end being adapted to being inserted into a sample container; and (d) a fluid sample transfer tubing having an inlet end and outlet end with the outlet end of the fluid sample transfer tubing being adapted for communicating with the inlet end of the internal transfer tubing of the NMR spectrometer and the inlet end being adapted to being inserted into a sample container, whereby said gas pressure is applied directly to said fluid sample.

2. The sample delivery system of claim 1 further comprising at least one sample container capable of maintaining an applied pressure and being adapted to the insertion of the outlet end of the gas transfer tubing and the inlet end of the sample transfer tubing.

3. The sample delivery system of claim 1 further comprising a second pressure controller having two ends, referred to as an inlet end and an outlet end, wherein the outlet end of the second pressure controller is adapted to providing fluid flow into and out of the outlet end of the internal transfer tubing of the NMR spectrometer and wherein the signal processor is further programmed to control pressure at the outlet end of the second pressure controller when a gas pressure is provided at the inlet end of the second pressure controller.

4. The sample delivery system of claim 3, wherein the outlet end of the second pressure controller is adapted to being directly attached to the outlet end of the internal transfer tubing of the NMR spectrometer.

5. The sample delivery system of claim 3, further comprising a collection container and a second gas transfer tubing having an inlet end and outlet end, wherein the inlet end of the second gas transfer tubing is attached to the outlet end of the second pressure controller and the outlet end of the second gas transfer tubing is inserted into the collection container which is capable of maintaining an applied pressure and is adapted to the insertion of the outlet end of the internal transfer tubing of the NMR spectrometer.

6. The sample delivery system of claim 1, further comprising a detector positioned along the internal transfer tubing of the NMR spectrometer to detect the movement of sample in the internal transfer tubing of the NMR spectrometer.

7. The sample delivery system of claim 6, wherein the detector is a UV detector.

8. A fluid sample delivery system for flow-through analysis in an NMR spectrometer, the spectrometer having (A) a magnet defining a magnetic field volume and (B) internal transfer tubing for passing a sample through the magnetic field volume and having an inlet end and an outlet end, the sample delivery system comprising:

(a) a first pressure controller having two ends, referred to as an inlet end and an outlet end;

(b) a second pressure controller having two ends, referred to as an inlet end and an outlet end, wherein the outlet end of the second pressure controller is adapted to providing fluid flow into and out of the outlet end of the internal transfer tubing of the NMR spectrometer;

(c) a signal processor programmed to control pressure at the outlet end of the first pressure controller when a gas pressure is provided at the inlet end of the first pressure controller and to control pressure at the outlet end of the second pressure controller when a gas pressure is provided at the inlet end of the second pressure controller, wherein the pressures are controlled in response to an input signal produced by the NMR spectrometer and detected by the signal processor;

(d) a gas transfer tubing having an inlet end and outlet end, with the inlet end of the gas transfer tubing being attached to the outlet end of the first pressure controller and with the outlet end being adapted to being inserted into a sample container; and (e) a fluid sample transfer tubing having an inlet end and outlet end with the outlet end of the sample transfer tubing being adapted to being attached to the inlet end of the internal transfer tubing of the NMR spectrometer and the inlet end being adapted to being inserted into a sample container.

9. The sample delivery system of claim 8 further comprising at least one sample container capable of maintaining an applied pressure and being adapted to the insertion of the outlet end of the gas transfer tubing and the inlet end of the sample transfer tubing.

10. The sample delivery system of claim 8, wherein the outlet end of the second pressure controller is adapted to being directly attached to the outlet end of the internal transfer tubing of the NMR spectrometer.

11. The sample delivery system of claim 8, further comprising a collection container and a second gas transfer tubing having an inlet end and outlet end, wherein the inlet end of the second gas transfer tubing is attached to the outlet end of the second pressure controller and the outlet end of the second gas transfer tubing is inserted into the collection container which is capable of maintaining an applied pressure and is adapted to the insertion of the outlet end of the internal transfer tubing of the NMR spectrometer.

12. The sample delivery system of claim 8, further comprising a detector positioned along the internal transfer tubing of the NMR spectrometer to detect the movement of sample in the internal transfer tubing of the NMR spectrometer.

13. The sample delivery system of claim 8, wherein the detector is a UV detector.

14. A method of achieving precise positioning of a fluid sample and improved signal to noise ratio in flow-through analysis in an NMR spectrometer, comprising a series of operations wherein:

(a) a fluid sample is provided;

(b) the fluid sample is tapped into;

(c) a gas pressure differential is applied directly to said fluid sample and is used to transfer the sample to a desired position within the NMR spectrometer;

(d) one or more NMR experiments is conducted; and (e) a gas pressure differential acting directly upon said fluid sample is used to transfer the sample out of the NMR spectrometer.

15. The method of claim 14, wherein the desired relative position of the sample is achieved by adjusting the pressure differential in response to signals detected by a signal processor.

16. A program storage device, readable by a signal processor of a fluid sample delivery system for flow-through analysis in an NMR spectrometer and programmed to control pressure at an outlet end of a pressure controller when a gas pressure is provided at an inlet end of the pressure controller, wherein the pressure is controlled in response to an input signal produced by the NMR spectrometer and detected by the signal processor and wherein the gas pressure acting directly upon said fluid sample is used to transfer a fluid sample into and out of the NMR spectrometer.

17. A fluid sample delivery system for flow-through NMR analysis in an NMR spectrometer, the spectrometer having (A) a magnet defining a magnetic field volume and (B) internal transfer tubing for passing a sample through the magnetic field volume and having an inlet end and an outlet end, the fluid sample delivery system comprising:

(a) a pressure controller having two ends, referred to as an inlet end and an outlet end;

(b) a signal processor;

(c) a program storage device readable by the signal processor and encoding instructions for controlling pressure at the outlet end of the pressure controller when a gas pressure is provided at the inlet end of the pressure controller, wherein the pressure is controlled in response to an input signal produced by the NMR spectrometer and detected by the signal processor;

(d) a gas transfer tubing having an inlet end and outlet end, with the inlet end of the gas transfer tubing being attached to the outlet end of the pressure controller and with the outlet end being adapted to being inserted into a sample container; and (e) a fluid sample transfer tubing having an inlet end and outlet end with the outlet end of the fluid sample transfer tubing being adapted for communicating with the inlet end of the internal transfer tubing of the NMR spectrometer and the inlet end being adapted to being inserted into a fluid sample container, wherein said gas directly acts upon said fluid sample to position said sample in said spectrometer.

* * * * *